(12) United States Patent
Schoebben et al.

(10) Patent No.: US 12,037,184 B2
(45) Date of Patent: Jul. 16, 2024

(54) ALUMINUM CONTAINER CONTAINING DICARBONATE

(71) Applicant: LANXESS Deutschland GmbH, Cologne (DE)

(72) Inventors: Karl-Joachim Schoebben, Dormagen (DE); Christoph Hofmann, Cologne (DE); Marcus Taupp, Monheim (DE); Erasmus Vogl, Bergisch-Gladbach (DE)

(73) Assignee: LANXESS Deutschland GmbH, Cologne (DE)

( * ) Notice: Subject to any disclaimer, the term of this patent is extended or adjusted under 35 U.S.C. 154(b) by 910 days.

(21) Appl. No.: 16/765,633

(22) PCT Filed: Nov. 16, 2018

(86) PCT No.: PCT/EP2018/081591
§ 371 (c)(1),
(2) Date: May 20, 2020

(87) PCT Pub. No.: WO2019/097005
PCT Pub. Date: May 23, 2019

(65) Prior Publication Data
US 2020/0277129 A1 Sep. 3, 2020

(30) Foreign Application Priority Data

Nov. 20, 2017 (EP) .................................... 17202540

(51) Int. Cl.
| | |
|---|---|
| *B65D 85/00* | (2006.01) |
| *B05D 1/02* | (2006.01) |
| *B05D 7/22* | (2006.01) |
| *B65D 23/08* | (2006.01) |
| *B65D 81/24* | (2006.01) |
| *C07C 69/96* | (2006.01) |

(52) U.S. Cl.
CPC ............... *B65D 85/70* (2013.01); *B05D 1/02* (2013.01); *B05D 7/227* (2013.01); *B65D 23/0821* (2013.01); *B65D 81/24* (2013.01); *C07C 69/96* (2013.01); *B05D 2202/25* (2013.01); *B05D 2508/00* (2013.01)

(58) Field of Classification Search
CPC .... B65D 85/70; B65D 23/0821; B65D 81/24; B05D 1/02; B05D 7/227; B05D 2202/25; B05D 2508/00; C07C 69/96
USPC .......................................................... 428/35.8
See application file for complete search history.

(56) References Cited

U.S. PATENT DOCUMENTS

| | | | |
|---|---|---|---|
| 3,186,906 A * | 6/1965 | Genth ....................... | A61L 2/20 514/512 |
| 3,936,269 A * | 2/1976 | Bayne ....................... | A23B 4/10 426/326 |
| 6,008,273 A | 12/1999 | Leibelt et al. | |
| 8,001,961 B2 | 8/2011 | Rudzinski et al. | |
| 8,142,858 B2 | 3/2012 | Cooke et al. | |
| 2014/0178616 A1* | 6/2014 | Richman ............ | C08G 18/4233 72/46 |

FOREIGN PATENT DOCUMENTS

| | | |
|---|---|---|
| CN | 204368790 U | 6/2015 |
| DE | 19912794 A | 9/2000 |
| DE | 102007045958 A1 | 4/2009 |
| JP | 05186404 | 7/1993 |
| JP | 2005093375 A2 | 4/2005 |

OTHER PUBLICATIONS

European Search Report from corresponding European Application No. EP17202540, dated May 4, 2018, three pages.

* cited by examiner

*Primary Examiner* — Brent T O'Hern
(74) *Attorney, Agent, or Firm* — Nicanor A. Kohncke; Christopher L. McDavid; Ewa M. Wozniak

(57) ABSTRACT

The invention relates to aluminium vessels containing dicarbonic diesters and to a method for producing the packaged dicarbonic diesters.

6 Claims, No Drawings

ALUMINUM CONTAINER CONTAINING DICARBONATE

The invention relates to aluminium vessels containing dicarbonic diesters and to a method for producing the packaged dicarbonic diesters.

Dicarbonic diesters, especially dimethyl dicarbonate and diethyl dicarbonate, are used in the beverage industry for the cold sterilization of alcohol-free carbonated or still fruit-juice drinks, fruit juices, wines, alcohol-free wines, ciders, ice teas and other beverages. This technology for beverage stabilization has a series of advantages. The reason for the outstanding advantage here lies in the fact that, in contrast to hot dispensing, there is no effect on flavour and colour. Relative to persistent preservatives as well, such as sodium benzoate/benzoic acid or potassium sorbate/sorbic acid, the advantage exists in particular in the absence of any adverse effects on flavour. Relative to cold aseptic dispensing, the quite substantially lower capital costs in plant technology, in particular, are a known advantage when using dicarbonic diesters.

Other applications of dicarbonic diesters have likewise been described, such as the inactivation of enzymes or use in batteries, for example.

A particular feature of the class of substance of the dicarbonic diesters, in contact with corresponding beverages, is that they undergo hydrolysis to form the derived alcohols and carbon dioxide. Typical examples of dicarbonic diesters are dimethyl dicarbonate, diethyl dicarbonate, diisopropyl dicarbonate, di-n-propyl dicarbonate or di-tert-butyl dicarbonate.

Depending on the temperature of the beverages during the application, therefore, the actual active substance is no longer present in the beverage after just a relatively short time. This is the case after a few hours at the customary temperatures of between 5 and 20° C. The hydrolysis, however, is also initiated by even the slightest amounts of water.

The decomposition of dicarbonic diesters is not confined only to hydrolysis; breakdown also occurs through spontaneous decarboxylation. This produces carbon dioxide and dialkyl carbonate. Since the stability of dimethyl dicarbonate is generally low and since fundamentally there is a tendency towards hydrolysis and decarboxylation, methods have been described for the stabilization of dicarbonic diesters during their preparation, storage and transport. In spite of the methods described, the storage and transport constitute an unresolved problem, since an uncontrolled and untimely decomposition results in the premature destruction of the dicarbonic diesters and to a build-up of pressure within the container. This may lead in turn to hazards associated with the handling of such containers in which the decomposition is occurring.

According to the prior art, dicarbonic diesters are customarily dispensed into glass vessels and transported in glass vessels. The stability of the dicarbonic diesters in glass vessels is satisfactory, and yet in their technical use there is often a restriction. For dimethyl dicarbonate for food use, for example, typical use-by dates amount to no more than 12 months. Extending the storage lives would be desirable. Moreover, the use of liquid substances in glass is always a problem, since glass easily breaks and, in the event of glass breakage, it is not possible to prevent leaks. For this reason, some of the glass vessels used are polymer-coated on the outside, but they are expensive to produce. According to the prior art, moreover, the glass vessel is transported in outer packaging of polystyrene, which again, however, is not only relatively expensive but also inconvenient.

In spite of these measures, a glass container must always be handled very carefully in order to prevent glass breakage, and this constitutes a major disadvantage.

Moreover, glass is problematic for storing chemicals which may give off gases, since excess pressure in the glass vessels may cause them to burst, and the airborne glass splinters may then constitute an additional safety risk for the employees. The polymeric outer layer of the glass vessels may also be attacked by heat or mechanical exposure.

A further packaging material known for substances of all kinds, besides glass, are metal vessels. Unfortunately, dialkyl dicarbonates decompose relatively quickly in all known metal vessels. On account of their low weight and their corrosion resistance, vessels made of aluminium in particular are known within the food sector. In order to improve the resistance to foods, a range of coated aluminium vessels have been described.

Known from U.S. Pat. No. 8,142,858 B2, for example, are vessels of aluminium metal which have been coated with epoxy resins or which have a multilayer system composed of polyester resins, polyvinyl chloride and polymethacrylate resins. These multiply coated containers are suitable for the transport and the storage of foodstuffs and beverages.

From U.S. Pat. No. 6,008,273 B2 it is known that epoxy resins or phenolic resins can be used to form water-resistant layers on metal bottles, including aluminium bottles in particular.

Known from U.S. Pat. No. 8,001,961 are aluminium bottles which can be coated with phenolic epoxy resins and are then used for transporting and storing gaseous anaesthetics that are sensitive to light.

Known from DE-A-19912794 are aluminium bottles which have been coated with mixtures of polyester resins and resole resins and are substantially free of bisphenol A diglycidyl ethers. These bottles are provided for filling with foods and beverages.

The disclosures also include methods for treating the dicarbonic diesters with the aim of improving the transport and storage properties. For example, U.S. Pat. No. 3,936,269 proposes a method wherein dimethyl dicarbonate is transported and stored in the frozen state and is thawed out again for use. In the frozen state, dimethyl dicarbonate is much more stable and storable, but its handling is much more complex technically and is therefore associated with high costs, and is not employed in practice.

In the existing transport and storage systems, the stability of dicarbonic diesters cannot be adequately guaranteed.

A problem which still needed addressing, therefore, was that of finding new transport containers for dicarbonic diesters that allow the disadvantages of the prior art to be overcome.

Surprisingly it has now been found that dicarbonic diesters can be stored and transported substantially without decomposition in aluminium vessels which are equipped on the inside with polymeric coatings.

A subject of the invention, therefore, is an aluminium vessel containing filled product, where the filled product comprises at least one compound of the formula (I) in which

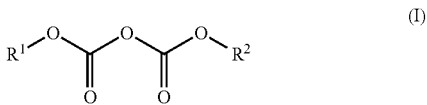

in which $R_1$ and $R_2$ independently of one another are straight-chain or branched $C_1$-$C_8$ alkyl, cycloalkyl, $C_2$-$C_8$ alkenyl, $C_2$-$C_8$ alkynyl or benzyl, which in each case is optionally substituted one or more times by identical or different halogen, nitro, cyano, $C_1$-$C_6$ alkoxy and/or dialkylamino substituents; or are phenyl which is optionally substituted one or more times by identical or different halogen, nitro, cyano, alkyl, haloalkyl, alkoxy, haloalkoxy, acyl, acyloxy, alkoxycarbonyl and/or carboxyl substituents, and the aluminium container is coated with at least one polymer, at least on the inside.

$R^1$ and $R^2$ independently of one another are preferably straight-chain or branched $C_1$-$C_8$ alkyl, $C_2$-$C_8$ alkenyl, phenyl or benzyl.

$R^1$ and $R^2$ independently of one another are more preferably straight-chain or branched $C_1$-$C_5$ alkyl, $C_3$ alkenyl or benzyl.

$R^1$ and $R^2$ independently of one another are very preferably methyl or ethyl.

More preferably still, the compounds of the formula (I) are dimethyl dicarbonate or diethyl dicarbonate or mixtures thereof.

The filled product generally constitutes compounds of the formula (I) or mixtures of the compounds of the formula (I). The filled product may likewise include further additions, such as inorganic or organic alkali metal salts or alkaline earth metal salts, siccatives, such as calcium chloride or silica gel, or oxygen scavengers, such as sulphites or phosphates, for example. The filled product preferably contains no further additions. The term "filled product" embraces the compounds to be transported and/or to be stored. The term "filled product" preferably does not embrace the inert gases or air which may additionally be present in the aluminium vessel. The compounds of the formula (I) or the mixtures of the compounds of the formula (I) are present preferably in an amount of 90 to 100%, based on the total amount of the filled product in the aluminium vessel. With particular preference the compounds of the formula (I) or the mixtures of the compounds of the formula (I) are present in an amount of 95 to 100%, very preferably in an amount of 98 to 100%, based on the total amount of the filled product, in the aluminium vessel. Even more preferably the compounds of the formula (I) are present in the aluminium vessel in an amount of 99 to 100%, based on the total amount of the filled product.

Aluminium vessels in the sense of the invention are all vessels which at least on the inside have an aluminium layer that can be coated with the polymer. The inside in the sense of the invention is that side of the aluminium vessel which via the polymer coating is in contact with the filled product. The outside of the vessel may also consist of another metal, or of an alloy or of plastic. The aluminium vessel preferably consists entirely of aluminium and possesses a polymer coating on the inside. The purity of the aluminium which is coated with the polymer is preferably >99%.

The polymer in the sense of the invention preferably comprises polyesters, phenolic resins, acrylic resins, amino resins or epoxy resins, which may also be used as mixtures.

Various commercially available polyesters are suitable for use in the present invention. Preferred for use as polyesters are VITE® polyesters (e.g. VITE® PE-100 and PE-200 saturated polyesters available from Goodyear Tire and Rubber Co., Akron, Ohio), URALAC® polyesters (e.g. URALAC® ZW5000SH, URALAC® SN978, URALAC® SN908 available from Royal DSM N.V.) and Dynapol® polyesters (e.g. Dynapol® LH and L, saturated polyester resins, available from Evonik Industries AG, Marl). Particularly preferred for use as polyester is URALAC® XP 8481 SN (Royal DSM N.V.).

The polyester preferably has an average molecular weight (MW) of 500 to about 10 000 g/mol, more preferably of 1000 to 7500 g/mol. The glass transition temperature (Tg) of the polyester is preferably greater than or equal to 50° C., more preferably greater than or equal to 60° C. With preference the glass transition temperature of the polyester is less than or equal to 100° C. The term "polyester" embraces polyesters which can be prepared from the same or different, i.e. mixed differing monomers. The polyester is typically prepared from polycarboxylic acids or anhydrides or mixtures thereof, and polyols. The polyester is prepared by known condensation and/or esterification processes, of the kind described, for example, in Zeno Wicks, Jr., Frank N. Jones and S. Peter Pappas, Organic Coatings: Wissenschaft and Technologie, vol. 1, pp. 122-132 (John Wiley and Sons: New York, 1992).

Preferred for use as polycarboxylic acids for preparing the polyesters are maleic acid, fumaric acid, succinic acid, adipic acid, phthalic acid, 5-tert-butylisophthalic acid, azelaic acid, sebacic acid, chlorendic acid, isophthalic acid, trimellitic acid, terephthalic acid, methyltetrahydrophthalic acid, methylhexahydrophthalic acid, tetrahydrophthalic acid, dodecanedioic acid, naphthalenedicarboxylic acid, pyromellitic acid and dimer fatty acids, cyclohexanedicarboxylic acid, such as, in particular, 1,4-cyclohexanedicarboxylic acid, glutaric acid, 12-hydroxystearic acid, 2-hydroxypropionic acid and 2-hydroxybutyric acid and mixtures thereof. Use is made with particular preference of dicarboxylic acids such as, in particular, phthalic acid, isophthalic acid, terephthalic acid, 1,4-cyclohexanedicarboxylic acid, succinic acid, sebacic acid, methyltetrahydrophthalic acid, methylhexahydrophthalic acid, tetrahydrophthalic acid, dodecanedioic acid, adipic acid, azelaic acid, naphthalenedicarboxylic acid, pyromellitic acid and dimer fatty acids.

As anhydrides, preference is given to using succinic anhydride, maleic anhydride, phthalic anhydride, tetrahydrophthalic anhydride, hexahydrophthalic anhydride, endomethylenetetrahydrophthalic anhydride, tetrachlorophthalic anhydride, trimellitic anhydride, pyromellitic dianhydride, and also the acid anhydrides of the polycarboxylic acids preferably employed, and their lower alkyl esters, such as more particularly their methyl esters. Preferred for use as lower alkyl esters of the polycarboxylic acids are dimethyl terephthalate, dimethyl succinate and dimethyl adipate.

As polyols it is possible with preference to use ethylene glycol, propylene glycol, 1,2- and 1,3-propanediol, diethylene glycol, dipropylene glycol, triethylene glycol, tetraethylene glycol, 1,4-butanediol, 1,3-butylethylpropanediol, 2-methyl-1,3-propanediol, 1,5-pentanediol, cyclohexanedimethanol, tricyclodecanedimethanol, glycerol, 1,6-hexanediol, neopentyl glycol, pentaerythritol, trimethylolethane, trimethylolpropane, 1,4-benzyldimethanol and -ethanol, 2,4-dimethyl-2-ethylhexane-1,3-diol, a polyethylene glycol or polypropylene glycol having an average molecular weight (Mw) of less than or equal to 500 g/mol, isopropylidenebis (p-phenyleneoxypropan-2-ol) and mixtures thereof. Polyols used with particular preference are diols. Preferred diols are ethylene glycol, propylene glycol, diethylene glycol, neopentyl glycol and mixtures thereof.

Particularly preferred for use as polyols are trimethylolpropane, neopentyl glycol, tricyclodecanedimethanol or 1,4-butanediol or mixtures thereof.

The polyester used preferably comprises hydroxyl or carboxyl groups as terminal functionalities. With particular preference the polyester used comprises hydroxyl groups as terminal functionalities. This is customarily achieved through the use of an excess amount of polyols during the esterification reaction.

As polymers in the sense of the invention it is also possible to use phenolic resins. The term "phenolic resins" encompasses phenolic resins which have been prepared from identical or different, i.e. mixed differing monomers. Phenolic resins used are the condensation products of aldehydes with phenols. Preferred for use as aldehydes are formaldehyde and acetaldehyde. Preferred for use as phenols are xylenol, cresol, p-phenylphenol, p-tert-butylphenol, p-tert-amylphenol and cyclopentylphenol. The phenolic resins which can be used preferably contain at least two or more reactive hydroxyl groups as functional groups, so that the phenolic resins can be crosslinked with the polyesters. The phenolic resins are preferably substantially free of bisphenol A (BPA), bisphenol F (BPF), bisphenol A diglycidyl ether (2,2'-bis(4-hydroxyphenyl) propane bis(2,3-epoxypropyl) ether) (BADGE) and bisphenol F diglycidyl ether (BFDGE).

In the sense of the invention, the term "substantially free of" means that the amount of the stated compounds is <5 ppm.

Phenolic resins used with particular preference are phenolic resins etherified with butanol. Preferred for use as phenolic resins are commercial phenolic resins such as, in particular, DUREZ® and VARCUM™ from DUREZ Corp. (Dallas, Tex.) or Reichhold Chemical AG (Austria); (CO) POLYMEROX™ from Monsanto Chemical Co. (St. Louis, MO); Arofene™ and Arotap™ from Ashland Chemical Co. (Dublin, Ohio); and BAKELITE® from Bakelite A. G. (Iserlohn, Germany) or Phenodur® PR 899, or Phenodur® PR515 or Phenodur® PR516 (Allnex GmbH), or mixtures of these phenolic resins.

Particularly preferred for use as phenolic resins are BAKELITE PF 6470 LB®, Bakelite 9989LB®, VARCUM 2227 B55®, Phenodur® PR 899, or Phenodur® PR515 or Phenodur® PR516, or mixtures of these phenolic resins.

As further polymers in the sense of the invention it is also possible to use epoxy resins. Preferred for use as epoxy resins are the reaction products from the reaction of phenols with epoxides. Used with particular preference are the epoxy resins from the reaction of bisphenol A, bisphenol F, phenol, butylphenol, xylenol and cresol with epichlorohydrin. Used even more preferably as epoxy resins are Epikote® 828 from Hexion GmbH, Germany.

As further polymers it is also possible to use polyacrylates. Polyacrylates in the sense of the invention are preferably polymethacrylates or polyacrylates of acrylic acid. These polyacrylates preferably contain functional groups, such as preferably carboxyl, hydroxyl or oxirane groups. Even more preferably the polyacrylates contain at least one carboxyl group or one oxirane-functional group, optionally in combination with one or more hydroxyl groups.

One preferred embodiment of the invention uses polyacrylates having an average molecular weight (MW) of 1000 to 50,000 g/mol, preferably of 2000 to 25,000 g/mol and more preferably of 5000 to 10,000 g/mol. The glass transition temperature of the polyacrylates is preferably in the range from −24° C. to 105° C. and more preferably in the range from 50° C. to 90° C.

The polyacrylate is preferably a copolymer of methacrylic acid (MA) and acrylic acid (AA) with ethyl methacrylate and butyl methacrylate, or a copolymer of 2-hydroxyethyl methacrylate (HEMA) with ethyl methacrylate, or a copolymer of glycidyl methacrylate (GMA) with ethyl methacrylate, or a copolymer of glycidyl methacrylate with hydroxypropyl methacrylate and styrene.

The polyacrylate is prepared by known chemical synthesis processes, for example by polymerization of ethylenically unsaturated acrylic monomers by means of radical polymerization.

In a further embodiment of the invention, the polymers are amino resins. Amino resins include the condensation products of aldehydes, such as formaldehyde, acetaldehyde, crotonaldehyde and benzaldehyde, with compounds which contain amino or amido group, such as urea, melamine and benzoguanidine. Preferred for use as amino resins are amino resins having two or more amino groups as functional groups.

Suitable amino resins are preferably benzoguanidine-formaldehyde polymers, melamine-formaldehyde polymers, esterified melamine-formaldehyde polymers and urea-formaldehyde polymers. The amino resin used is preferably the fully alkylated melamine-formaldehyde polymer which is obtainable commercially from Cytec Industries (Cytec Industries GmbH, Neuss, Germany) under the tradename CYMEL® 303.

In a further embodiment of the invention, the polymers are crosslinked. Any suitable crosslinker containing hydroxyl, amino, vinyl or isocyanate groups can be used. In one preferred embodiment the polymers, such as especially amino resins, phenolic resins or epoxy resins, serve as crosslinkers.

In a further embodiment of the invention, the polymers may likewise be crosslinked by isocyanate groups. Preferred for use as isocyanates are aliphatic and cycloaliphatic polyisocyanates, such as, preferably, hexamethylene diisocyanate (HDI), isophorone diisocyanate (IPDI), bis[4-isocyanatocyclohexyl]methane (TMXDI), tetramethylene-m-xylidine diisocyanate (H 12 MDI), isopropenyldimethylbenzyl isocyanate (TMI), dimers or trimers thereof, and mixtures thereof. Suitable commercially available isocyanate crosslinkers are preferably VESTANAT® B 1358 A, VESTANAT® EP B 1186 A, VESTANAT® EP B 1299 SV (Evonik Resource Efficiency GmbH, Marl, Germany) and DESMODUR® BL 3175 (Bayer AG, Leverkusen, Germany).

The polymers can be used without further auxiliaries, especially if the polymers are liquid at room temperature and under atmospheric pressure, or are mixed with further organic solvents, lubricants, catalysts, pigments and additives. For the purposes of this invention, the term "polymer compositions" is used to designate polymers in the presence or absence of further organic solvents, lubricants, catalysts, pigments and additives. Preferred polymer compositions are those which comprise polymers in the presence of further organic solvents, lubricants, catalysts, pigments and/or additives.

Organic solvents used which are particularly useful as carrier liquids for the polymers are preferably aliphatic hydrocarbons, such as, for example and preferably, solution benzine, kerosene and P naphtha; aromatic hydrocarbons, such as especially benzene, toluene, xylene or solvent naphtha 100, 150, 200 (Exxon Chemicals GmbH); alcohols, such as especially ethanol, n-propanol, isopropanol, n-butanol or isobutanol; ketones such as especially 2-butanone, cyclohexanone, methyl aryl ketones, ethyl aryl ketones or methyl isoamyl ketones; esters, such as especially ethyl acetate or butyl acetate; glycols, such as especially butyl glycol, glycol ethers, such as especially methoxypropanol; glycol ethers, such as especially ethylene glycol monomethyl ether, ethylene glycol monoethyl ether, ethylene glycol monobutyl ether, propylene glycol monomethyl ether; glycol esters, such as especially butyl glycol acetate or methoxypropyl acetate, or mixtures thereof. Particular preference is given to using solvent naphtha 100, 150 or 200 or mixtures thereof. Solvent naphtha is also known under the trade name Solvesso™.

Catalysts can be used in order to increase the rate of curing or crosslinking.

Catalysts used are preferably quaternary ammonium compounds, phosphorus compounds, compounds of tin and of zinc, such as preferably tetraalkylammonium halide, a tetraalkylammonium or tetraarylphosphonium iodide or acetate, tin octoate, zinc octoate, triphenylphosphine or mixtures thereof.

Particularly preferred for use as catalysts are phosphoric ester solutions, such as preferably ADDITOL XK 406™ (Cytec Surface Specialties, Inc., West Paterson, NJ) or sulfonic acids, such as preferably CYCAT 600™ (Cytec Surface Specialties, Inc., West Paterson, NJ) or mono- and dioctyltin mercaptides, such as preferably Tinstab OTS 17 MS™ (AKZO-Nobel Chemicals, Inc., Chicago, Ill.) or dibutyltin dilaurate, such as preferably FASCAT™ (Atofina Chemicals, Inc., Philadelphia, Pa.) or mixtures of these catalysts.

In one preferred embodiment, the catalyst is used in an amount of 0.05 wt % to 5 wt %, preferably in an amount of 0.1 to 1.5 wt %, based on the weight of the polymer composition.

The polymer compositions may comprise lubricants. Preferred for use as lubricants are long-chain aliphatic waxes, such as especially carnauba waxes (Luba-Print 887/C-wax dispersion, Münzing Chemie GmbH, Abstatt, Germany), synthetic wax dispersions, such as preferably Lanco™ GLIDD 4518V (Lubrizol Corp., Wickliffe, Ohio), Lanco™ Wax TF 1780 EF, Lanco™ Wax 1350 FF (Lubrizol Corp., Wickliffe, Ohio), polyethylene, polypropylene, lanolin, polytetrafluoroethylene and mixtures of these compounds.

Pigments as well may be added to the polymer composition. Suitable pigments, such as aluminium flakes, titanium dioxide and zinc oxide, are customarily used in order to enhance the appearance of the protective layer. Where aluminium flakes are used as pigments, they are employed preferably in an amount of 2 wt % to 15 wt % and more preferably in an amount of 5 wt % to 10 wt %, based on the weight of the polymer composition. A pigment such as titanium dioxide will be used preferably in an amount of 35 wt % to 50 wt % and more preferably in an amount of 40 wt % to 45 wt %, based on the weight of the polymer composition. Where zinc oxide is used as pigment, it is present preferably in an amount of 0.5 wt % to 30 wt %, and more preferably in an amount of 5 wt % to 15 wt %, based on the weight of the polymer composition.

With particular preference the amount of pigments in the polymer composition is less than 300 ppm. Very preferably the amount of pigments in the polymer composition is less than 50 ppm. More preferably still, the polymer composition contains no pigments.

The matter of whether the polymer composition may include further additives, such as water, surfactants, dispersants (preferably lecithin), defoamers (preferably modified polysiloxanes), thickeners (preferably methylcellulose), or fillers, such as preferably silicates or aluminium/magnesium hydroxides, and also magnesium oxide, calcium oxide or carbon black, or mixtures thereof, is particular on the particular application.

With particular preference the amount of fillers in the polymer composition is less than 300 ppm. Very preferably the amount of fillers in the polymer composition is less than 50 ppm. More preferably still, the polymer composition contains no fillers.

The polymer composition is produced preferably by simple mixing of the polymer and all the optional constituents in any desired order and with adequate stirring. The resulting mixture is mixed preferably until all of the constituents of the composition are substantially homogeneously mixed. The polymer composition is produced preferably at temperatures of between 10° C. and 50° C.

The polymer composition is applied preferably in liquid form, as a solution, suspension or dispersion, to the aluminium surface. Application may be performed by spreading, dipping, rolling or spraying or by comparable techniques. The suspension is preferably applied by spraying to the aluminium surface of the vessel.

If it is applied as a liquid coating, the polymer composition preferably has a solids content of 25 wt % to 70 wt % non-volatile material and more preferably of 30 wt % to 50 wt % non-volatile material.

In one preferred embodiment the polymer composition contains 20 wt % to 80 wt % of polyesters and 1 wt % to 80 wt % of organic solvents and less than 1 wt % of lubricants and/or catalysts.

In another preferred embodiment the polymer composition contains 20 wt % to 75 wt % of polyesters, 10 wt % to 79 wt % of organic solvents and 1 wt % to 25 wt % of other polymers, such as especially polyacrylates, epoxy resins, phenolic resins or amino resins, and less than 1 wt % of lubricants and/or catalysts.

In another preferred embodiment the polymer composition contains 20 wt % to 75 wt % of polyesters, 10 wt % to 79 wt % of organic solvents and 1 wt % to 25 wt % of phenolic resins, and less than 1 wt % of lubricants and/or catalysts.

In another preferred embodiment the polymer composition contains 20 wt % to 75 wt % of polyesters, 10 wt % to 79 wt % of organic solvents and 0.9 wt % to 25 wt % of phenolic resins and 0 to 2 wt % of catalysts and 0.1 to 2 wt % of lubricants.

In another preferred embodiment the polymer composition contains 20 wt % to 75 wt % of polyesters, 10 wt % to 79 wt % of organic solvents and 0.9 wt % to 25 wt % of phenolic resins and 0 to 2 wt % of catalysts and 0.1 to 2 wt % of lubricants and less than 5 ppm of fillers and/or pigments.

In another preferred embodiment the polyester has been prepared at least on the basis of pyromellitic dianhydride, tricyclodecanedimethanol and the crosslinker isophorone diisocyanate. This polyester and the crosslinker are present in particular in the products Goldlack 32S23MC and Goldlack BT651B from Valspar Corp., Minneapolis, Minn., USA. Aluminium vessels coated with this varnish and in which the filled product has been in contact with the Goldlack 32S23MC or/and Goldlack BT651B are easily cleaned with aqueous solutions. In this cleaning operation, the varnish detaches from the aluminium surface.

The process of curing the polymer composition on the surface is accomplished preferably by heating, preferably at a temperature of 150° C. to 280° C. The heating time is preferably 1 min to 10 min.

The polymer compositions can be applied to aluminium sheets on an industrial scale by methods known to the skilled person, such as, for example, by the so-called sheet bake method using roll coating, the coil coating method, or by strip coating, or else by spraying methods. The polymer composition is then cured by exposure to heat, actinic radiation, by means of ultraviolet or infrared light, for example, by electromagnetic radiation, such as electron beam curing, or through a combination of these methods. The coated sheets can then be shaped into vessels. It is, however, likewise possible, and also preferable, for the completed aluminium vessels to be coated with the polymer composition, preferably by spraying. The polymer composition on the surface is cured preferably by heating.

The polymer coatings formed on the aluminium surface have a thickness of preferably 1 to 50 μm. With particular preference the polymer coatings have a thickness of 5 to 10 μm.

The scope of the invention embraces all of those radical definitions, parameters and elucidations given above and set out below, whether they be general or stated in preference ranges, with one another, hence also between the respective ranges and preference ranges, in any desired combination.

The invention likewise embraces a method for producing an aluminium vessel containing filled product, containing at least one compound of the formula (I)

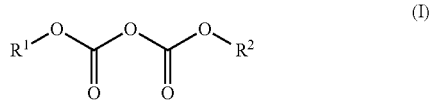

(I)

in which $R_1$ and $R_2$ independently of one another are straight-chain or branched $C_1$-$C_8$ alkyl, cycloalkyl, $C_2$-$C_8$ alkenyl, $C_2$-$C_8$ alkynyl or benzyl,
which in each case is optionally substituted one or more times by identical or different halogen, nitro, cyano, $C_1$-$C_6$ alkoxy and/or dialkylamino substituents; or are phenyl which is optionally substituted one or more times by identical or different halogen, nitro, cyano, alkyl, haloalkyl, alkoxy, haloalkoxy, acyl, acyloxy, alkoxycarbonyl and/or carboxyl substituents,
wherein in a step a.) an aluminium vessel is coated with a polymer composition and in a step b.) this layer is cured and then in a step c.) the product, optionally under inert gas, is filled into this aluminium vessel.

The product is filled into the interior of the aluminium vessel preferably by means of a filling nozzle. This dispensing operation takes place preferably under inert gas. Examples of suitable inert gases include argon, helium and nitrogen. A preferred inert gas used is nitrogen. After filling has taken place, the opening is sealed preferably by means of a plastic cap, available for example from Bericap at Budenheim, Del.. The plastic caps may contain further inserts, such as sealing disks based on polytetrafluoroethylene (PTFE), for example. An insert of this kind is available commercially under the name "Plytrax 100" from Norton Performance Plastic Corporation, Wayne, NJ, USA. In this model, the PTFE layer in the cap is fastened to the cap by means of a polyethylene foam.

The filled product can generally be stored and transported at temperatures and pressures which appear to the skilled person to be suitable. Storage and transport take place preferably at temperatures of between −78° C. and +40° C., more preferably at temperatures of between −38° C. and +38° C. and very preferably at −25° C. to +25° C. The filled product is stored and transported preferably at atmospheric pressure, meaning that no special pressure is mandated. The storage and the transport of the filled product may take place in the presence or absence of an inert gas. Storage and transport in the presence of an inert gas are preferred. A preferred inert gas used is nitrogen.

As a result of the special, coated aluminium vessels, the compounds of the formula (I) can be stored in a purity of more than 97% over a period of one to three years. With particular preference the compounds of the formula (I) can be stored in a purity of more than 98% over a period of up to 2 years. Very particularly, the compounds of the formula (I) can be stored in a purity of more than 99% over a period of up to 2 years.

The filled product-containing aluminium vessel is preferably attached to commercial metering pump systems. This enables the filled product to be metered easily into other vessels, preferably containing beverages, or into beverage lines. The invention, therefore, likewise embraces the use of the filled product-containing aluminium vessel in metering pump systems for transfer and metering into other vessels or into beverage lines.

Under the inventive use of the aluminium vessels, the compounds of the formula (I) can be transported and stored without substantial decomposition. In the packaging hitherto customary, such as glass containers, for example, used for transportation, in contrast, a considerable breakdown of the active substance within a short time is observed. Because the weight of aluminium vessels is much lower by comparison with their glass counterparts, the transport costs of the compounds of the formula (I) can be reduced by virtue of the inventive use of the aluminium vessels. Moreover, the containers are not deformable by heat, and reliably protect the contents from exposure to light. The aluminium vessels used in accordance with the invention can likewise be recycled.

EXAMPLES

Example 1

Production of the Coated Aluminium Vessel

A polyester resin varnish (Goldlack BT651B (from Valspar Corp.)) was applied by spraying to the aluminium surface, more particularly to the surface facing the filled product. The vessel was then heated at 190° C. for 10 min. Thereafter the uniformity of the coating was examined optically.

Example 2

Filling of the Aluminium Vessel With Dimethyl Dicarbonate

The coated aluminium bottles from Example 1 are filled with dimethyl dicarbonate and sealed directly with a plastic cap from Bericap, Budenheim. The caps have a polytetrafluoroethylene (PTFE) seal. The seal is available commercially under the name "Plytrax 100" and was obtained from Norton Performance Plastic Corporation, Wayne, NJ, USA.

Example 3

Stability Tests of Dimethyl Dicarbonate In Different Containers 3 kg of dimethyl dicarbonate were filled into different containers, available commercially and produced experimentally, as listed in Table 1, and the containers were then sealed and placed for storage into various temperature cabinets. The conditions, in other words the storage time and the storage temperature, under which the filled product was stored in the containers can be seen from Table 1. Analysis was carried out by gas chromatography; in this case, a determination was made of the amount of dimethyl carbonate present, which is a breakdown product in the thermal decomposition of dimethyl dicarbonate. Where a high quantity of dimethyl carbonate is found, this is representative of a low stability of the dimethyl dicarbonate.

TABLE 1

| | Storage temperature [° C.] | Dimethyl carbonate content [ppm]/after X days' storage |
|---|---|---|
| Aluminium, uncoated (from Leicht und Appelt, Bad Gandersheim, GER) | 20 | 6724 ppm/35 days |
| Aluminium anodized (from Leicht und Appelt, Bad Gandersheim, GER) | 20 | 4462 ppm/35 days |
| Glass | 20/40/20* | 19 591 ppm/168 days |
| Polyester resin varnish, coated on aluminium, with a pigment content of less than 300 ppm. (Goldlack BT651B (from Valspar Corp. AG, Grüningen, CH) | 20/40/20* | 120 ppm/365 days |
| Polyester resin varnish coated on aluminium, with a pigment content of less than 300 ppm. (Goldlack 32S23MC (from Valspar Corp. AG, Grüningen, CH) | 20/40/20* | 840 ppm/365 days |

*5 weeks' storage at 20° C., then 4 weeks at 40° C., then continued storage at 20° C.

As can be seen from Table 1, dimethyl dicarbonate can be stored for much longer, and hence more stably, in aluminium vessels coated with polyester varnish than in uncoated or anodized aluminium vessels.

What is claimed is:

1. An aluminium vessel having a product contained therein, comprising: an inside containing the product therein, wherein the product comprises at least one compound selected from the group of dimethyl dicarbonate and diethyl dicarbonate,
and wherein said inside is coated with a polymer layer that comprises at least one polymer which is a polyester prepared from at least a pyromellitic dianhydride, a tricyclodecanedimethanol and a crosslinker comprising isophorone diisocyanate.

2. The aluminium vessel according to claim 1, wherein the at least one compound fills the vessel in an amount of 90 to 100%, based on a total amount by volume of products filling the vessel.

3. The aluminium vessel according to claim 1, further comprising fillers and/or pigments, wherein the amount of fillers and/or pigments is less than or equal to 50 ppm of the polymer layer.

4. The aluminium vessel according to claim 1, wherein the polymer layer has a thickness of 5 to 10 μm.

5. The aluminium vessel according to claim 1, wherein the at least one polymer has an average molecular weight (MVV) of 1000 to 7500 g/mol.

6. The aluminium vessel according to claim 1, wherein the at least one polymer is a polyester having a glass transition temperature of less than or equal to 100° C.

* * * * *